US00PP35893P3

(12) United States Plant Patent
Olesen

(10) Patent No.: US PP35,893 P3
(45) Date of Patent: Jul. 2, 2024

(54) ROSE PLANT NAMED 'POULREN046'

(50) Latin Name: *Rosa hybrida*
Varietal Denomination: Poulren046

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,493

(22) Filed: Sep. 8, 2023

(65) Prior Publication Data

US 2024/0107925 P1 Mar. 28, 2024

(30) Foreign Application Priority Data

Sep. 30, 2022 (QZ) ..... PBR 2022/2156

(51) Int. Cl.
*A01H 5/02* (2018.01)
*A01H 6/74* (2018.01)

(52) U.S. Cl.
USPC ..... Plt./139
CPC ..... *A01H 6/749* (2018.05)

(58) Field of Classification Search
USPC ..... Plt./130, 137, 139
See application file for complete search history.

*Primary Examiner* — Susan McCormick Ewoldt
*Assistant Examiner* — Zachariah Allan Kay

(57) ABSTRACT

A new garden rose plant of the Hybrid Tea class which has abundant, pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulren046'.

This application claims priority to Plant Breeder's Rights Application Number 2022/2156, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulren046', originated as a single seedling from the stated cross.

The new variety may be distinguished from its male pollen parent and female seed parent primarily by the following characteristics. The male pollen parent plant has light pink flowers and grows to a height of 60 cm while the new variety has pink flowers and grows to a height of 72 cm. The female seed parent plant has small pink flowers about 50 mm in diameter while the new variety has large pink flowers, about 80 mm in diameter.

The objective of the hybridization of this rose variety was to create a new and distinct variety with unique qualities, such as:

1. Uniform and abundant pink perfumed flowers;
2. Vigorous, but compact growth when propagated on its own roots;
3. Exceptional disease resistance.

This combination of qualities is not present in previously available commercial cultivars of this type, known to the inventor, and distinguish 'Poulren046' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulren046' was selected in the spring of 2015 by the inventor as a single plant from the progeny of the aforementioned hybridization.

Asexual reproduction of 'Poulren046' by rooted cuttings was first done by Mogens N. Olesen in the nursery in Fredensborg, Denmark in July, 2015. This initial and other subsequent asexual propagations conducted in controlled environments have demonstrated that the characteristics of 'Poulren046' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren046'.

Specifically illustrated in FIG. 1 of the drawings are a cluster of flower buds and open flowers on a branch, sepals detached revealing reproductive flower parts, and flower petals detached.

Figure 1:
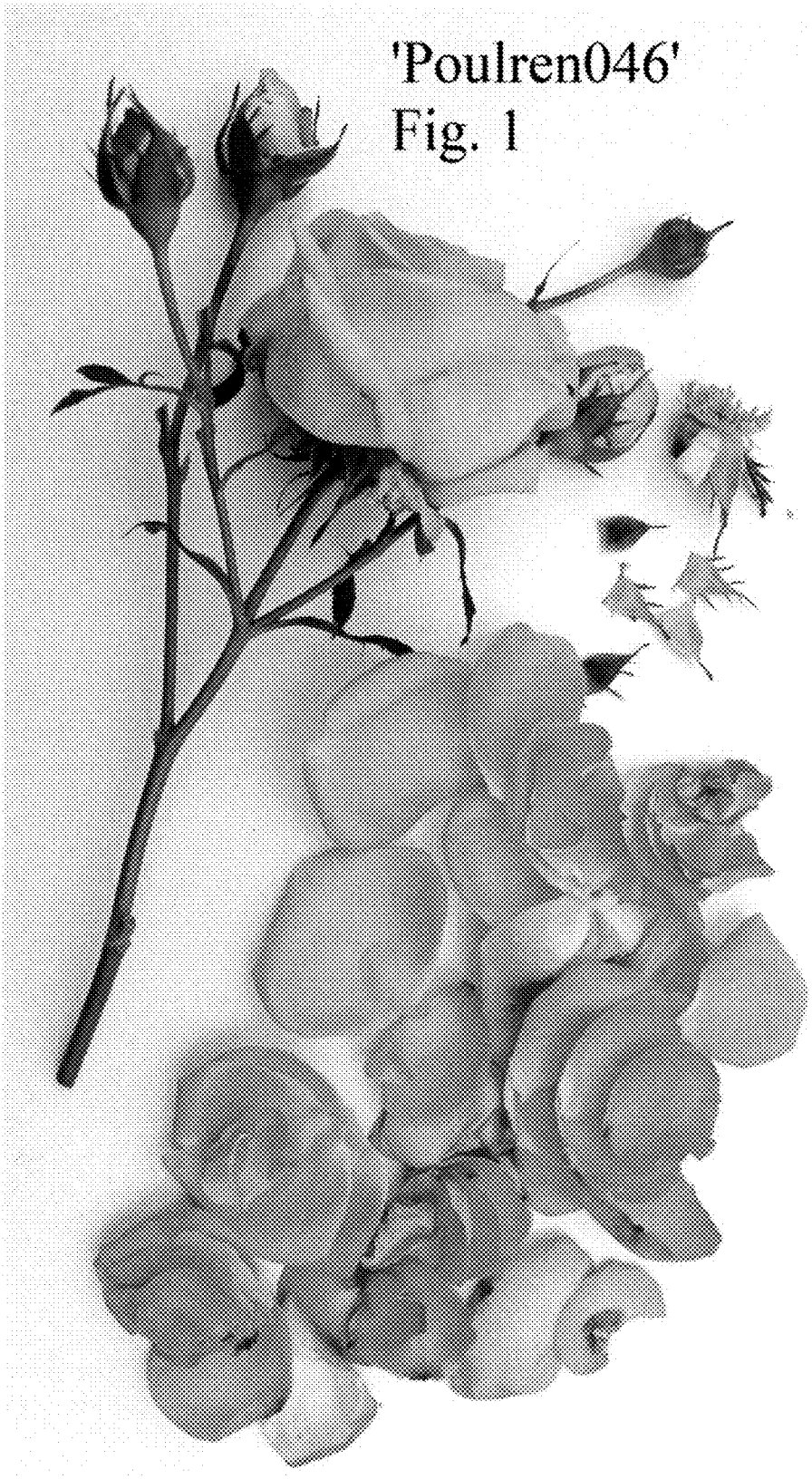
Figure 2:
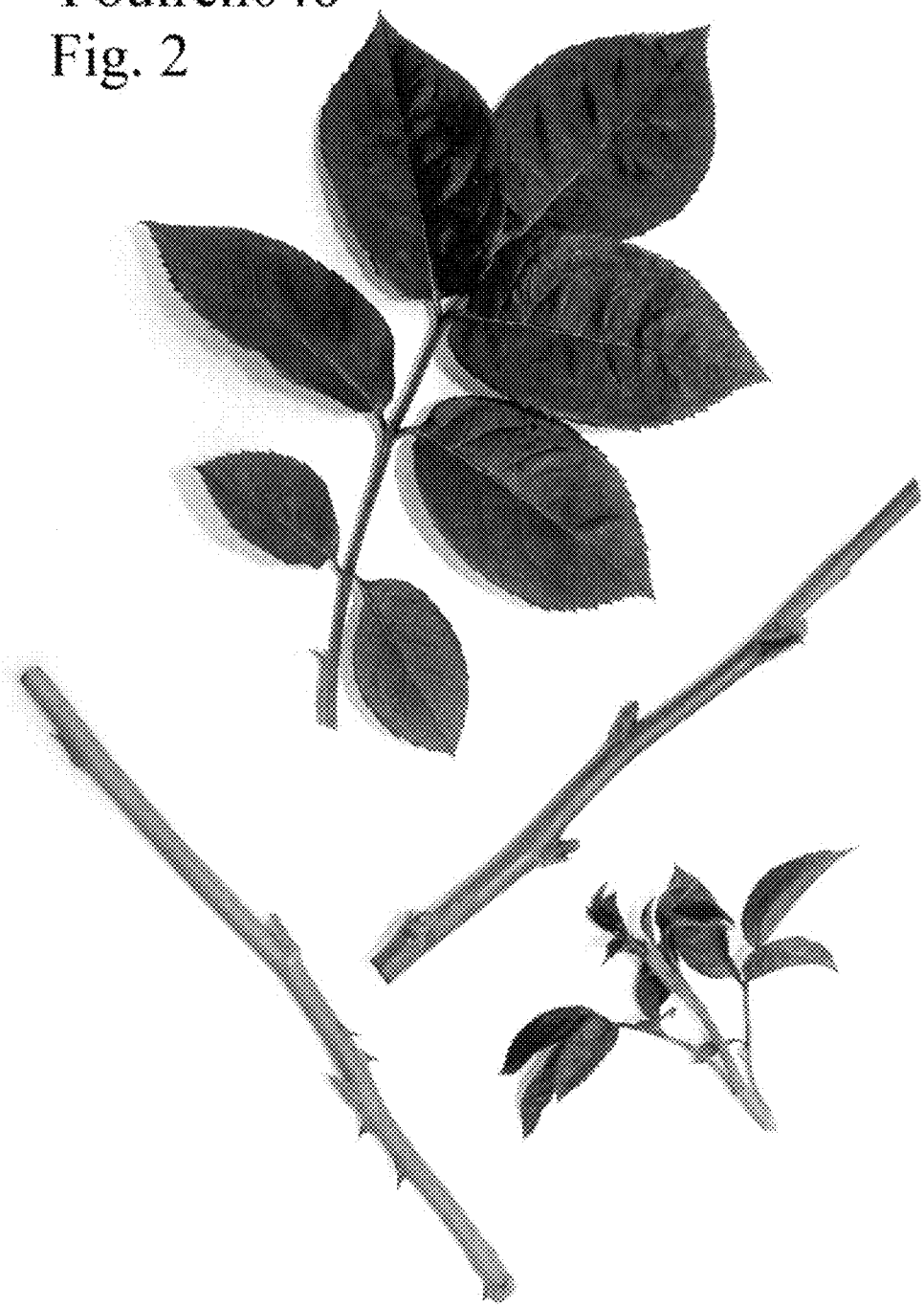

Specifically illustrated in FIG. 2 of the drawings is a mature compound leaf, mature bare stem, juvenile stem, and juvenile leaves exhibiting anthocyanin.

Plants shown are 15 months in age.

DETAILED DESCRIPTION OF THE VARIETY

The following is a description of 'Poulren046', as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulren026', U.S. Plant Pat. No. 30,751 are compared to the claimed plant. While 'Poulren046' has 55 flower petals, 'Poulren026' has 20 flower petals. The claimed plant has a flower diameter of 80 mm while 'Poulren026' has a flower diameter of 90 to 100 mm. Open flowers of 'Poulren046' are generally Red Group 49A in color while 'Poulren026' has a general tonality of Red Group 43D.

Flower and Flower Bud

Blooming habit: Continuous.

Flower bud:

- *Size.*—Upon opening, 24 mm in length from base of receptacle to end of bud. Bud diameter is 11 mm.
- *Bud form.*—Ovoid.
- *Sepal inner surface.*—Color: Yellow-Green Group 146D. Surface: Lightly pubescent.
- *Sepal outer surface.*—Color: Yellow-Green Group 144A with strong intonations of Greyed-Purple Group 183C. Texture: Smooth.
- *Sepal shape.*—Apex: Cirrhose. Base: Flat at union with receptacle.
- *Sepal margin.*—Margins have moderate strong foliaceous appendages on three of the five sepals.
- *Sepal size.*—24 mm long, 11 mm wide.
- *Receptacle.*—Texture: Smooth. Size: 10 mm in height, 11 mm wide. Color: Yellow-Green Group 144A. Shape: Between funnel and campanulate.
- *Pedicel.*—Surface: Rough with many stipitate glands. Length: About 30 to 35 mm. Diameter: 2 to 3 mm on average. Color: Yellow-Green Group 145A Greyed-Red Group 180C. Strength: Strong.
- *Peduncle.*—Length: 40 to 90 mm. Diameter: About 3 mm. Color: Yellow-Green Group 145A. Texture: Smooth.

Flower bud development: Flower buds are borne in clusters of 5 flower buds per stem.

Flower bloom:

- *Fragrance.*—Very strong perfume with hints of pine.
- *Duration.*—The blooms have a duration on the plant of approximately 18 days. Petals fall cleanly away from plant after flowers have fully matured.
- *Size.*—Flower diameter is about 80 mm when fully open. Flower depth is 46 mm.
- *Flower shape.*—Flat topped rosette with many slightly overlapping petals of different sizes.
- *Shape of flower, side view.*—The upper portion is flat. The lower portion is concave.

Petalage: Under normal conditions, flowers have about 55 petals.

General tonality of flower: Open flowers are Red Group 43D. Tonality does not fade as the flower ages.

Petal color:

- *Upon opening, outer petals.*—Upper surface: Red Group 52D. At basal zone small spot Yellow Group 4C. Lower surface: Basal and middle zone are Red Group 56D. The margins have intonations of Red Group 54B. At the base of the petal there is a medium sized petal spot Yellow 1D.
- *Upon opening, inner petals.*—Upper surface: Red Group 43B with streaks of White Group 155 B. Petal spot at the basal zone Yellow Group 4B. Lower surface: Red Group 48C with a Yellow Group 4B petal spot.
- *After opening, outer petals.*—Upper surface: Red Group 48D. At the basal point of attachment, a medium sized spot Yellow Group 4C. Lower surface: Red-Purple Group 65D with shades of Red Group 56B.
- *After opening, inner petals.*—Upper surface: Red Group 48D with a basal zone spot of Yellow 4C. Lower surface: Red-Purple Group 65D with shades of Red Group 56B.

Petals:

- *Petal reflex.*—Partially reflexed.
- *Margin.*—Mostly entire, however some have one or more clefts in the margin. Light undulations.
- *Shape.*—Broad and elliptic. Apex shape: Rounded. Base shape: Acute.
- *Size.*—About 60 mm (l)×60mm (w).
- *Texture.*—Smooth.
- *Thickness.*—Average.

Petaloids:

- *Size.*—About 32 mm (l) by 13 mm (w).
- *Quantity.*—Between 5 and 10.
- *Shape.*—Elliptical with an acute base and rounded apex.
- *Color.*—Red Group 43B on the upper surface with a petaloid spot at the basal zone Yellow to Group 4B. The undersurface is Red Group 48C with a Yellow Group 4B petaloid spot.

Reproductive flower parts:

- *Pollen.*—None observed.
- *Anthers.*—Size: 2 mm in length. Color: Greyed-Yellow Group 160D. Quantity: 65 on average.
- *Filaments.*—Color: Yellow Group 13D. Length: 11 mm.
- *Pistils.*—Length: 5 mm. Quantity: 60 on average.
- *Stigmas.*—Color: Greyed-Yellow Group 160D.
- *Styles.*—Color: Red Group 47C.
- *Location of stigmas.*—Inferior in location relative to the length of the filaments and the height of the anthers.
- *Hips.*—None Observed.

Plant

Plant growth: Upright. Plants are about 72 cm in height, and 60 cm wide.

Stems:

- *Color of juvenile growth.*—Yellow-Green Group 146B with intonations of Greyed-Red Group 180B.
- *Color of mature growth.*—Yellow-Green Group 146A with intonations of Greyed-Red Group 180B.
- *Length.*—Canes are about 35 cm from the base of the plant to the flowering portion.
- *Diameter.*—About 6 mm.
- *Internodes.*—On mature canes about 35 to 40 mm between nodes.
- *Surface texture.*—Young wood: Smooth. Older wood: Smooth.

Long prickles:

- *Incidence.*—1 or 2 prickles per 10 cm of stem.

*Size.*—Average length of prickles on mature stems is 8 mm.

*Shape.*—Upper portion is linear. Lower portion is concave.

*Color.*—Juvenile prickles: Greyed-Red Group 182B. Mature prickles: Greyed-Purple Group 183B.

Plant foliage:

*Compound leaf.*—About 210 mm (l)×150 mm (w).

*Quantity.*—2 leaves per 10 cm of stem on average.

*Leaf bearing angle to the stem.*—45 degrees.

*Color of juvenile foliage.*—Upper side: Yellow-Green Group 146C with intonations of Greyed-Purple Group 183B. Lower side: Yellow-Green Group 144B.

*Color of mature foliage.*—Upper side: Yellow-Green Group 147A. Lower side: Yellow-Green Group 147B.

Plant leaves and leaflets:

*Stipules.*—Size: 20 mm long, 2 mm wide. Quantity: 2 per compound leaf. Shape: Linear, slightly broad based with outward extending apex. Margins: Finely serrated. Color: Yellow-Green Group 144A.

*Petiole.*—Length: About 35 mm. Diameter: 2 mm. Upper surface color: Yellow-Green Group 144A. Lower surface color: Yellow-Green Group 144A.

*Rachis.*—Length: About 90 mm. Upper surface color: Yellow-Green Group 144A. Lower surface color: Yellow-Green Group 144A.

*Leaflet.*—Quantity: Normally 7 leaflets. Margins: Serrated. Size: Terminal leaflets are about 84 mm long, 52 mm wide. Shape: Generally elliptical. Base: Rounded. Apex: Acuminate. Texture: Rugose. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in The American Horticulture Society heat zone 7.

I claim:

1. A new and distinct variety of rose plant named 'Poulren046' substantially as described and illustrated herein.

* * * * *

'Poulren046'

'Poulren046'